United States Patent
Xu et al.

(10) Patent No.: US 9,868,716 B2
(45) Date of Patent: Jan. 16, 2018

(54) METHOD FOR PREVENTING AND/OR TREATING A SUBJECT SUFFERING FROM ASTHMA

(71) Applicants: Hong Kong Baptist University, Kowloon (HK); Shanghai University of Traditional Chinese Medicine, Shanghai (CN)

(72) Inventors: Hongxi Xu, Shanghai (CN); Yue Lv, Shanghai (CN); Wenwei Fu, Shanghai (CN); Kaixian Chen, Shanghai (CN); Zhaoxiang Bian, Kowloon (HK); Shilin Chen, Kowloon (HK); Dajian Yang, Kowloon (HK); Aiping Lu, Kowloon (HK); Sun Chi Albert Chan, Kowloon (HK)

(73) Assignees: HONG KONG BAPTIST UNIVERSITY, Kowloon Tong, Kowloon (HK); SHANGHAI UNIVERSITY OF TRADITIONAL CHINESE, Shanghai (CN)

( * ) Notice: Subject to any disclaimer, the term of this patent is extended or adjusted under 35 U.S.C. 154(b) by 0 days.

(21) Appl. No.: 14/824,763

(22) Filed: Aug. 12, 2015

(65) Prior Publication Data

US 2016/0185744 A1 Jun. 30, 2016

(30) Foreign Application Priority Data

Dec. 25, 2014 (CN) .......................... 2014 1 0841469

(51) Int. Cl.
*C07D 311/86* (2006.01)
(52) U.S. Cl.
CPC ................... *C07D 311/86* (2013.01)
(58) Field of Classification Search
None
See application file for complete search history.

(56) References Cited

PUBLICATIONS

Lu et al. "The Natural Compound Nujiangexanthone A Suppresses Mast Cell Activation and Allergic Asthma". Biochemical Pharmacology. 2016; 100:61-72 (Published Online Nov. 10, 2015).*
Xia et al. "Bioassay-Guided Isolation of Prenylated Xanthones and Polycyclic Acylphloroglucinols from the Leaves of Garcinia nujiangensis". Journal of Natural Products. 2012; 75:1459-1464.*
Wei et al. "Small Molecule Antagonists of Tcf4/Beta-Catenin Complex Inhibit the Growth of HCC Cells in Vitro and in Vivo". Int. J. Cancer. 2010; 126:2426-2436.*
Wellcome Trust Sanger Institute [Online]. "The Measure of Man". [Retrieved Feb. 5, 2013]. Retrieved from the Internet: <URL: http://www.sanger.ac.uk/about/press/2002/021205.html.> Published Dec. 5, 2002.*
Bischoff SC. "Role of Mast Cells in Allergic and Non-Allergic Immune Responses: Comparison of Human and Murine Data". Nature Reviews Immunology. 2007; 7:93-104.*
Bradding et al. "The Role of the Mast Cell in the Pathophysiology of Asthma". J Allergy Clin Immunol. 2006; 117:1277-1284. (Year: 2006).*

* cited by examiner

*Primary Examiner* — Leslie A. Royds Draper
(74) *Attorney, Agent, or Firm* — Idea Intellectual Limited; Margaret A. Burke; Sam T. Yip

(57) ABSTRACT

A compound of formula (I) or a pharmaceutically acceptable salt, hydrate or prodrug thereof for inhibiting Syk activity,

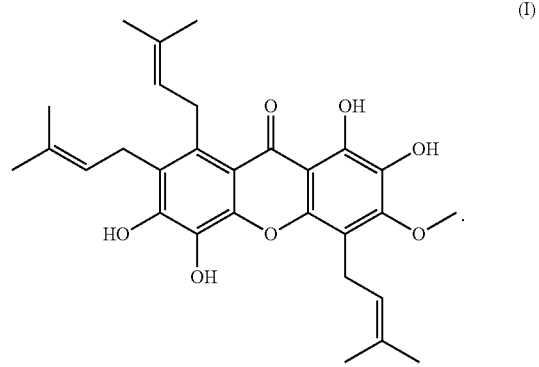

(I)

4 Claims, 9 Drawing Sheets

METHOD FOR PREVENTING AND/OR TREATING A SUBJECT SUFFERING FROM ASTHMA

TECHNICAL FIELD

The present invention relates to a compound for inhibiting spleen tyrosin kinase (Syk) activity, and more particularly to a flavonoid obtained from *Garcinia nujiangensis* for inhibiting Syk activity.

BACKGROUND

Protein kinase is the largest family of human kinase and contains over 500 proteins. Spleen tyrosine kinase (Syk) is a member of Syk family of tyrosine kinase, and is a regulator for the development of B cells at early stage. Syk also regulates the activation, signal transduction and lifespan of mature B cells.

Syk is a non-receptor tyrosine kinase which plays a critical role in immunoreceptor and integrin-mediated signal transduction in various cells including B cells, macrophages, monocytes, mast cells, eosinophils, basophils, neutrophils, dendritic cells, T cells, natural killer cells, thrombocytes and osteoclasts. The immunoreceptors described herein include typical immunoreceptors and molecules similar to immunoreceptors. Typical immunoreceptor includes B cells, T cell antigen receptors and various immunoglobulin receptors (Fc receptor). Molecules similar to immunoreceptors may relate to a structure of the immunoreceptor, or may participate in a similar signal transduction pathway with the typical immunoreceptor. Also, these molecules mainly take part in non-adaptive immune response such as activation of neutrophils, natural killer cell recognition and osteoclast activity. Integrin is a cell surface receptor which plays a critical role in leukocyte adhesion and activation, in both congenital immunity and adaptive immunity.

Binding of the ligand activates both immunoreceptor and integrin, and results in a phosphorylation of an immunoreceptor tyrosine-based activation motif (ITAM) in cytoplasmic surface of a receptor associated transmembrane adaptin. The activation activates Src family kinase. Syk combines with the phosphorylated ITAM of an adaptin to tirgger Syk activation and the subsequent phosphorylation and downstream signaling pathway activation.

Syk is essential to the activation of B cells by B cell receptor (BCR) signal transduction. Syk is activated when binding to the phosphorylated BCR. Thereby, early signal transduction event occurs after BCR activation. The B cell signal transduction through BCR may result in a wide range of biological yield, which depends on the stage of development of B cells. The magnitude and duration of a BCR signal have to be regulated accurately. Abnormal BCR-mediated signal transduction could cause disordered B cell activation and/or result in production of autoantibodies causing multiple-autoimmune diseases and/or inflammatory diseases. Syk-deficient mice show impaired mature B cells, reduced production of immunoglobulin, compromised T cell irrelevant immune response, and significant degradation of persistent calcium signal in BCR stimulation.

Functions of B cells and humoral immune system in etiology of autoimmunity and/or inflammatory disease have been evident with substantial proofs. A protein-based therapy (such as Rituxan) developed for complete depletion of B cells provides an approach for treating many autoimmune diseases and inflammatory diseases. It is known that the autoantibodies and the immune complex produced therefrom function as a pathogen in autoimmune diseases and/or inflammatory diseases. Pathogenic responses on these antibodies rely on a signal transduction through a Fc receptor which depends on Syk. Since Syk is involved in B cell activation and FcR dependent signal transduction, an inhibitor of Syk can thus be used as an inhibitor for inhibiting B cell-mediated pathogenic activity which is caused by autoantibodies. Therefore, it is suggested that the suppression of Syk enzyme activity in cells exerts effect on autoantibodies and thus can be used for treating autoimmune disease.

Syk also plays a pivotal role in FcεRI-mediated mast cell degranulation and activation of eosinophils. Therefore, Syk is also involved in allergic disorder such as asthma. Syk binds to the phosphorylated Y chain of FcεRI through its SH2 domain. Syk is necessary for downstream signal transduction. Syk-deficient mast cells show impaired degranulation, arachidonic acid and cytokine secretions. Therapeutic agents used for suppressing Syk activity in mast cells also show the above conditions. The therapy using Syk antisense oligonucleotide suppresses permeation of antigen induced eosinophils and neutrophils in asthma animal model. Syk-deficient acidophil cells also show impaired activation because of response to FcεRI stimulation. Therefore, small molecule inhibitors for inhibiting Syk are useful for treating allergy-induced inflammatory diseases such as asthma.

Syk is also very important to the functions of mast cells and mononuclear cells. For example, Syk deficiency in mice is related to the impaired IgE-mediated mast cells activation. The IgE-mediated mast cells activation significantly reduces the release of TNFα and other inflammatory cytokines. Also, it is shown that Syk kinase inhibitor suppresses mast cell degranulation in cell-based analysis. In addition, it has been shown that Syk inhibitor suppresses antigen-induced Passive Cutaneous Anaphylaxis (PCA), bronchoconstriction and bronchoedema in rats.

Therefore, the suppression of Syk activity can be used for treating and/or preventing Syk-associated diseases. Specifically, the suppression of Syk activity can be used for treating allergic disorders, autoimmune diseases and inflammatory diseases, such as systemic lupus erythematosus (SLE), rheumatoid arthritis, multiple polyangitis, idiopathic thrombocytopenic purpura (ITP), myasthenia gravis, allergic rhinitis, chronic obstructive pulmonary disease (COPD), adult respiratory distress syndrome (ARDS) and asthma. In addition, Syk plays a key role in ligand-independent nourishing signal transduction, which is known to be important survival signal transduction in B cells. Thus, inhibition of Syk activity can be used for treating certain cancers including B cell lymphomas and leukemia.

SUMMARY OF THE INVENTION

In accordance with a first aspect of the present invention, there is provided a compound of formula (I) or a pharmaceutically acceptable salt, hydrate or prodrug thereof for inhibiting Syk activity in a subject,

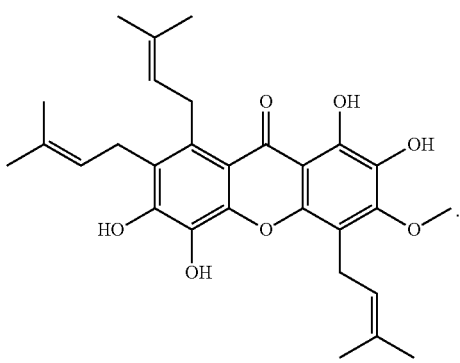

(I)

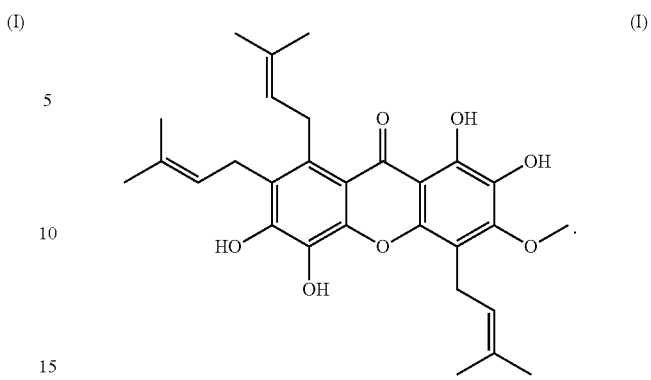

(I)

In accordance with a second aspect of the present invention, there is provided a method for treating and/or preventing Syk-associated disease, comprising: administering an effective amount of a compound of formula (I) or a pharmaceutically acceptable salt, hydrate or prodrug thereof to a subject

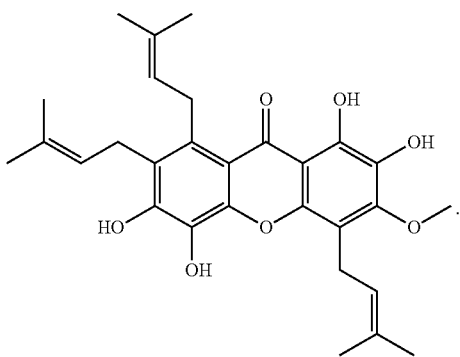

(I)

In one embodiment of the second aspect, the effective amount of the compound is adminstered to a mast cell of the subject.

In one embodiment of the second aspect, the Syk-associated disease may be inflammatory disorder such as asthma, autoimmune disease, or cancer such as leukemia or B cell lymphomas.

In one embodiment of the second aspect, the effective amount of the compound in a pharmaceutical composition is around 0.0001-50 wt %.

In one embodiment of the second aspect, the composition is administered to the subject with a dosage of 0.001-50 mg/kg body weight/day.

In accordance with a third aspect of the present invention, there is provided a pharmaceutical composition for treating and/or preventing Syk-associated disease in a subject, comprising a compound of formula (I) or a pharmaceutically acceptable salt, prodrug, hydrate or a mixture thereof, In one embodiment of the third aspect, the Syk-associated disease may be inflammatory disorder such as asthma, autoimmune disease, or cancer such as leukemia or B cell lymphomas.

In one embodiment of the third aspect, the compound is around 0.0001-50 wt % in the composition.

BRIEF DESCRIPTION OF THE DRAWINGS

Embodiments of the present invention will now be described, by way of example, with reference to the accompanying drawings in which.

DETAILED DESCRIPTION

Figure 1A:
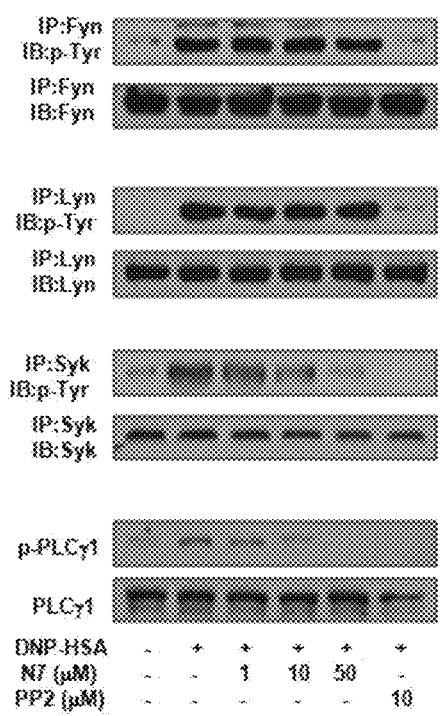
FIG. 1a shows the effect of Nujiangexanthone A (N7) on the phosphorylation of Syk, Fyn and Lyn under the pretreatment of N7 and Src family inhibitors in murine mast cells.

In the description, the following terms generally have the following definitions, unless otherwise specified.

The term "therapeutically effective amount" or "effective amount" refers to the valid amount that can achieve a therapeutic effect such as relieving symptoms, slowing disease progression or preventing disease when the compound of the present invention is administered to human or non-human patients. For example, a therapeutically effective amount can be the amount that is sufficient to reduce the extent of symptoms of diseases which respond to the inhibition of Syk activity. In some embodiments, the therapeutically effective amount is the amount that is sufficient to reduce symptoms of cancers, the symptoms of allergic disorders, autoimmune diseases and/or inflammatory diseases or acute inflammatory responses. In some embodiments, the therapeutically effective amount is the amount that is sufficient to reduce the number of tumor cells, slow down or stop the growth of tumors in a detectable level. In some embodiments, the therapeutically effective amount is the amount that can reduce the size of the tumor. In some conditions, patients with cancer may not have obvious symptoms. In some embodiments, the therapeutically effective amount is the amount that is sufficient to prevent a significant increase in detectable level of the cancer or cancer marker levels in the patient's blood, serum or tissue, or is sufficient to reduce the above levels. According to the treatment of allergic disorders and/or autoimmune diseases and/or inflammatory diseases and/or acute inflammation of the present invention, the therapeutically effective amount can be the amount that is sufficient to slow down the progression of the diseases or to prevent the symptoms of allergic disorders and/or autoimmune diseases and/or inflammatory diseases and/or acute inflammation of the patients. According to the treatment of allergic disorders and/or autoimmune diseases and/or inflammatory diseases and/or acute inflammation of the present invention, the therapeutically effective amount can be the amount that is sufficient to decrease the amount of protein markers or cell types in patient's blood or serum. For example, in some embodiments, the therapeutically effective amount is the amount of compound of the present invention that can significantly lower the activity of mast cells.

The term "inhibition" indicates a significant decrease in the baseline activity of a biological activity or process.

"Inhibition of Syk activity" refers to the decrease of Syk activity when directly or indirectly affected by the compound of the present invention, as compared with the Syk activity when the compound of the present invention has not been applied. The decrease of activity can be attributed to the direct interaction between the compound of the present invention and Syk or the interaction between the compound of the present invention and one or more factors affecting the Syk activity. For example, the compound of the present invention can decrease the activity of Syk by directly binding with Syk, and by (directly or indirectly) causing another factor to decease the activity of Syk or by (directly or indirectly) decreasing the amount of Syk in cells or organisms.

The term "activity of mast cells" includes activities that mast cells secret a variety of cytokines, release particles and substances in the particles by cell disruption, and participates in an immune response.

The term "inhibition of activity of mast cells" refers to the decrease of the activity of mast cells when directly or indirectly affected by the compound of the present invention, as compared with the activity of mast cells in the absence of the compound of the present invention. The decrease of the activity can be attributed to the interaction between the compound of the present invention and Syk, or one or more other factors, which can affect the activity of Syk.

The term "allergy" or "allergic disorder" refers to a subject being allergic to substances (allergens). Allergic conditions include eczema, allergic rhinitis, asthma, urticaria, food allergies and other atopic status.

The term "asthma" refers to respiratory system disorders which are characterized by the increase of inflammation, narrowing of lung airways and increase of the activity of lung airways to inhaling reagents. Asthma is highly, but not merely, related to atopic or allergic symptoms.

The term "diseases reactive to the inhibition of Syk activity" refers to the diseases which can therapeutically benefit from inhibiting the activity of Syk kinase. The therapeutic benefits include relieving symptoms, slowing disease progression, preventing or delaying onset of the disease, or inhibiting abnormal activity of specific cells (mast cells).

The term "treatment" refers to the administration of the compounds of the present invention to treat, reduce, slow the progress, change, heal, affect, or improve the disease or symptoms of the disease or prognostic of disease.

The term "patient" refers to animals, which are or will be the subject of the treatment, observation or experiment, such as a mammal. The method of the present invention can be used in both human therapy and veterinary applications. In some embodiments, the patients are mammals; in some embodiments, the patients are humans; in some embodiments, the patients are mice.

The present invention is based on an unexpected discovery that Nujiangexanthone A obtained from *Garcinia nujiangensis* can inhibit the activation of mast cells and other corresponding inflammatory responses by regulating Syk-mediated signal transduction. Thus, this compound can be prepared as a medicament or health care product for preventing or treating diseases which are responsive to the inhibition of Syk signal transduction.

Nujiangexanthone A obtained from *Garcinia nujiangensis* comprises the following formula:

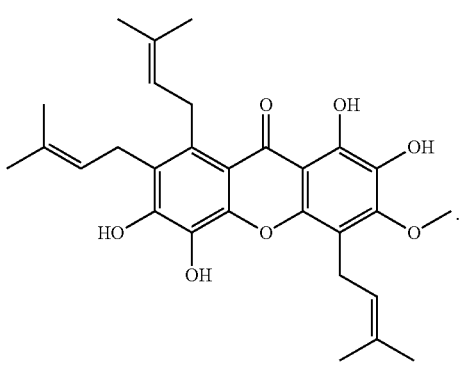

(I)

The compound of the present invention can be obtained from *Garcinia nujiangensis* by any common methods in the art such as simple extraction by alcohol, chromatography and so forth. The compound of the present invention can also be obtained commercially or synthesized from commercially available starting materials by conventional synthesis. One of ordinary skill in the art can synthesize the compound of the present invention by any known techniques. The synthesized compound of the present invention can be further purified by chromatography, high performance liquid chromatography (HPLC) or crystallization.

The compound of the present invention includes, but is not limited to, its optical isomers, racemates and other mixtures. In those cases, the individual enantiomers or non-enantiomers, i.e. optically active forms, can be obtained by asymmetric synthesis or by resolving the racemates. Resolving racemates can be accomplished by crystallization in the presence of a resolving agent or by high performance liquid chromatography (HPLC) through a chiral column. In addition, such compounds include Z- and E-forms (or cis and trans forms) having carbon-carbon double bond. The compound of the present invention has various tautomeric forms, which include all tautomeric forms of the compounds. The compounds also include crystalline forms of polymorphs and inclusion.

The compound of the present invention also includes its crystalline and amorphous forms. These forms comprise polymorph, pseudo polymorphs, solvates, hydrates, unsolvated polymorphs (including anhydride), conformation polymorph and amorphous forms and mixtures thereof. "Crystalline form" and "polymorph" and "novel form" in the present invention may be interchangeable and are intended to include all crystalline and amorphous forms of the compound of the present invention. These forms include polymorphs, pseudo polymorphs, solvates, hydrates, unsolvated polymorphs (including anhydride), conformational polymorphs, and amorphous forms and mixtures thereof, unless the form of the compound is mentioned as a specific crystalline or amorphous form. The compound of the present invention includes pharmaceutically acceptable forms of the compound, including forms of chelates, non-covalent complexes, prodrugs, and mixtures thereof.

"Pharmaceutically acceptable salts" includes, but is not limited to, salts of inorganic acids such as hydrochloride, phosphate, diphosphate, hydrobromide, sulfate, sulphite, nitrate and the like; salts of organic acids such as malate, maleate, fumarate, tartrate, succinate, citrate, acetate, lactate, methanesulfonate, p-toluenesulfonate, 2-isethionate, benzoate, salicylate, stearate, and salts of carboxylic acid such as acetate, $HOOC-(CH_2)_n-COOH$, wherein $n=0\sim4$ and the like. Similarly, pharmaceutically acceptable cations include, but are not limited to, sodium, potassium, calcium, aluminum, lithium and ammonium.

Furthermore, if the compound of the present invention is obtained form an acid salt, free alkali can be obtained by an alkalization of the solution of the acid salt. Conversely, if the product is a free alkali, according to the process of preparing an acid salt from an alkali, a salt, especially a pharmaceutical salt, can be prepared by solvating the free alkali by a suitable organic solvent and treating the solution by an acid. One of ordinary skill in the art acknowledges various synthetic methods that can be used for preparing non-toxic pharmaceutically salt.

As described above, prodrugs also fall within the ambit of the compound of the present invention. In some embodiments, the "prodrugs" of the present invention includes any compounds which can be converted to the compound of the present invention during metabolic processing after the "prodrugs" are administered to the patient. In some embodiments, prodrugs include the derivatives of the compound of the present invention having a functional group such as a carboxylic group. For example, prodrugs include, but are not limited to, esters such as alkyl esters, hydroxyalkyl esters, arylalkyl esters, and aryloxyalkyl esters.

"Solvates" are formed by the interaction between a solvent and a compound. The term "compound" includes solvates of compounds. Similarly, the term "salt" includes solvates of salts. Suitable solvates are pharmaceutically acceptable solvates, such as a hydrate comprising a monohydrate and a hemihydrate.

"Chelates" are formed by bonding a compound to metal ions at two or more points. The term "compound" includes chelates of the compound of the present invention. Similarly, "salts" also include chelates of the salts.

"Non-covalent complexes" are formed by a compound and another molecule, wherein covalent bonding is not formed between the compound and the molecule. For example, complexation can occur by way of van der Waals' interaction, hydrogen bondings and electrostatic attraction (i.e. ionic bondings). The term "compound" also comprises such "non-covalent complexes".

The present invention further provides a pharmaceutical composition. The pharmaceutical composition comprises the compound of the present invention and a pharmaceutically acceptable carrier, and the pharmaceutical composition can be used for inhibiting Syk signaling pathway.

The content of the compound of the present invention in a pharmaceutical composition is, for instance, 0.0001-50 wt %; preferably 0.001-30 wt %; more preferably 0.01-20 wt %. The therapeutically effective amount of the pharmaceutical composition of the present invention is between 0.001-500 mg/kg body weight/day, any amount within the range should be considered as the effective amount of the pharmaceutical composition of the present invention; preferably, the therapeutically effective amount of the pharmaceutical composition of the present invention is between 0.005-300 mg/kg body weight/day; more preferably, the therapeutically effective amount of the pharmaceutical composition of the present invention is between 0.01-100 mg/kg body weight/day. The term "therapeutically effective amount" is used to refer to a single therapy or a combined therapy of a relevant disease. One of ordinary skill in the art understands that the actual dosage can be greater or smaller than the range given above. The "therapeutically effective amount" of a certain patient (such as mammals or humans) and specific treatment solutions can be affected by many factors, such as the pharmacological activities of the compound or the prodrugs of the present invention, age, body weight, general situations, gender, diet of the patients, as well as the time of administration, disease susceptibility, disease progression, the judgment of the physician and so forth.

The compound or the composition of the present invention can be adminstered by oral, intravenous, intramuscular, subcutaneous, intranasal, rectal and other routes. The solid carrier includes, for instance, starch, lactose, phosphate, glycols, microcrystalline cellulose, brown sugar and kaolin, and the liquid carrier comprises, sterile water, polyethylene glycols, nonionic surfactants and edible oils (such as corn oil, peanut oil and sesame oil). All of the above can be used if they suit the properties of the active component and certain administration routes. Adjuvants, which are commonly used in the preparation of pharmaceutical compositions, can also be used. The adjuvants include, for instance, flavorings, colorings, preservatives and antioxidants such as vitamin E, vitamin C, BHT and BHA.

The compound of the present invention can also be adminstered parenterally or intraperitoneally. The solution or suspension of the active compounds (as the ionized base or a pharmaceutically acceptable salt thereof) can be prepared in water mixed with surfactants (e.g. hydroxypropylcellulose). The dispersion can also be prepared in glycerin, polyethylene and mixture in the oil. Under general storage and usage conditions, these reagents include preservative for preventing the growth of microorganisms.

The pharmaceutical forms suitable for injection include: sterile aqueous solutions or dispersions and sterile powders (for immediate preparation of sterile injectable solutions or dispersions). In all conditions, the forms should be sterile and must be in a liquid form such that it can be discharged by a syringe. The forms should be stable during manufacturing process and storage and are prevented from contaminations and influence of microorganisms such as bacteria and fungi. The carrier can be a solvent or a dispersion medium containing water, alcohols, suitable mixtures thereof, and vegetable oils.

The present invention will become apparent from the detailed description given below. Features, purposes and advantages of the present invention are described by the following description and claims.

The present invention is described by specific embodiments in the following paragraphs. One should understand that the embodiments are used to illustrate, but not limit, the present invention. Any unidentified conditions of the experiment methods can be accomplished by common condition or conditions suggested by the manufacturers. The percentage, ratios, parts are measured in weight unless specifically indicated.

Unless specifically stated, the terms in the present invention are identical with the scientific terms in the technical field. In addition, all similar or equivalent methods or materials can be used in the method of the present invention. The preferred method and the material described herein are merely described as examples.

Features described above or features described in embodiments can be arbitrarily combined. All the features in the present invention can be used with any form of combination. The features in the description can be replaced by the same, equivalent, or alternative characteristics with similar purposes. Therefore, unless specifically mentioned, the disclosed features are only general examples of equivalent or similar features.

Embodiment 1 Nujiangexanthone A (N7) Inhibits Signal Transduction Pathways of Murine Mast Cells 1.1 Materials 6-well plate purchased from Denmark Thermo NUNC Co.

RPMI1640 (high glucose) fetal calf serum, penicillin and streptomycin purchased from Invitrogen Corporation in US.

1.2 Methods 1.2.1 Cell Culture

Bone marrow-derived mast cells (BMMC) of mice were separated from BALB/c murine marrow and were cultured in RPMI1640 liquid containing IL-3, 10% of calf serum, 100 U/ml of penicillin and 100 µg/ml of streptomycin for 6 weeks. Two markers c-kit and FceRI on cell membranes were detected by using flow cytometric analysis. When double-positive cells detected, having both markers, have exceeded 95%, the cultured cells can be used for the experiment.

1.2.2 Western Blot

Cells were treated with Nujiangexanthone A (N7) in corresponding concentrations for 5, 15 and 30 minutes. The samples were collected and lysed. The samples were then separated by 8% gel in sodium dodecyl sulfate polyacrylamide gel electrophoresis (SDS-PAGE) and transferred to polyvinylidene fluoride (PVDF) membrane. The following antibodies were used to analyze the samples: ERK, JNK, p38, IKK, IkBa, NF-kB and so forth. If the compound is found to interfere with the expression and phosphorylation of the target proteins, a corresponding specific inhibitor may be used to conduct a comparative analysis.

1.2.3 Immunoprecipitation

Mast cells were pre-treated with IgE overnight, and were washed by PBS thrice. After re-suspended with medium, they were treated with different concentrations of Nujiangexanthone A for 1 hour. Dinitrophenyl human serum albumin (DNP-HSA) was used to treat the cells for 5 minutes. A/G agarose was added into the cell lysates and the mixtures were rotated at a rotator for 1 hour. Antibodies of Syk, Fyn and Lyn were added, and the mixtures were rotated overnight. On the following day, PBS was used to wash the complex of magnetic beads, antibody and protein for 5 times. A Western Blot loading dye was added into the complex and the mixtures were boiled for 5 minutes. The samples were tested by Western Blot, and the phosphorylated antibody of tyrosine was used to treat the samples. In the experiment, a specific inhibitor PP2 of Src family was used as a positive control for comparative analysis.

1.3 Results

Figure 1B:
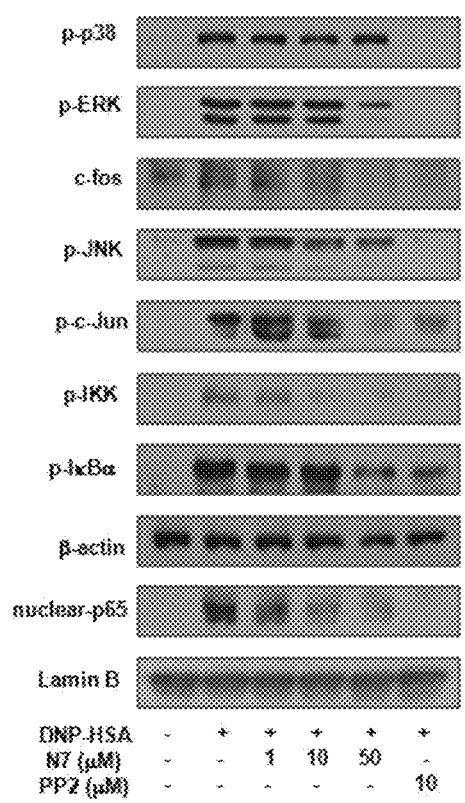
FIG. 1b shows the Western Blot analysis of the downstream signaling pathways of Syk, including MAPKs, NF-kB and AP-1, after the pretreatment of N7 and Src family inhibitors in murine mast cells.

The experimental results are shown in FIGS. 1a and 1b. The results of FIG. 1a are obtained by pretreating the antibody-treated mast cells with N7 and Src family inhibitor PP2 for 1 hour and then treating the cells with antigens for 5 minutes. Phosphorylation of Syk, Fyn and Lyn were then examined by immunoprecipitation. The results of FIG. 1b are obtained by pretreating the antibody-treated mast cells with N7 and Src family inhibitor PP2 for one hour and then treating with antigens for 15 minutes. The downstream signal pathways of Syk including MAPKs, NF-kB and AP-1 were then analyzed by Western Blot.

As shown by the immunoprecipitation results, Nujiangexanthone A (N7) selectively inhibits the phosphorylation of the upstream signaling molecule Syk of mast cells without affecting Src family members Fyn and Lyn. Syk, Fyn, and Lyn are the most important signal promoters to the upstream signaling pathway of mast cells. The phosphorylation of Syk can induce various downstream signal pathways such as MAPK, NF-kB and so forth. Fyn can stimulate Syk and Lyn can stimulate PI3K signaling pathway. According to the results of the present invention, Nujiangexanthone A does not affect the phosphorylation of Fyn and Lyn but significantly inhibits the phosphorylation of Syk, such that the transduction of the downstream signaling pathways is inhibited. By separating tissues of cytoplasm and nucleus, the effect of Nujiangexanthone A on expression and phosphorylation of inflammatory signaling proteins was examined by Western Blot. Nujiangexanthone A inhibits MAPK signaling pathways, such that the production of transcription factors AP-1 (c-Jun+c-fos) which is mediated by MAPK is inhibited. Nujiangexanthone A also inhibits NF-kB signal pathways and thus inhibits the nuclear translocation of p65.

Embodiment 2 Nujiangexanthone A (N7) Inhibits the Production of Cytokines in Spleen and the Activation of Signaling Molecules in Spleen Cells 2.1 Materials Phosphorylated Syk, Stat6, Zap70 and T-bet, GATA3 antibodies purchased from cell signaling Co.

2.2 Methods 2.2.1 Tissues Collection

Lymph nodes and spleen of mice were collected. The collected tissues were respectively grinded, counted and cultivated. The cultured tissues were stimulated with PMA and ionomycin for 48 hours. The supernatant and the cells were then collected for analysis. The supernatant was used for examining various cytokines, and the cells were used for measuring expressions of various T cell specific proteins by Western blot.

2.2.2 Statistical Analysis

Experimental data are all expressed by mean value±standard error. The data were analyzed by statistics software Graphpad Prism 5 with One-Way ANOVA analysis. Dunnet's test was used for pairwise comparisons. $P<0.05$ indicates a standard for statistically significant difference.

2.3 Results

Figure 2A:
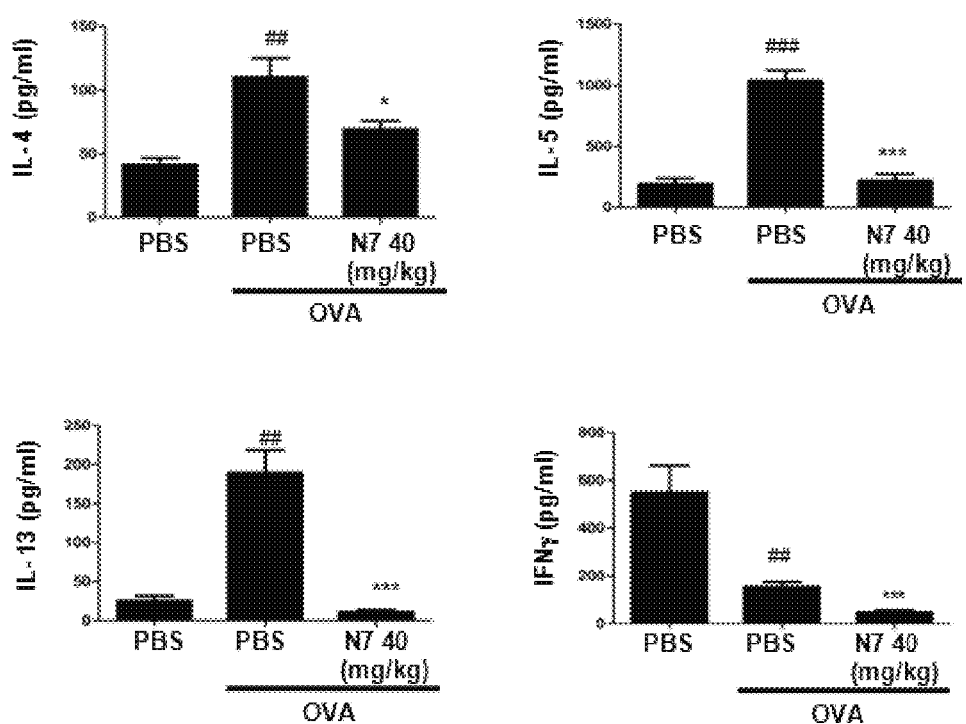
FIG. 2a shows the ELISA analysis on cytokines IL-4, IL-5, IL-13 and IFNγ of murine spleen cells after different treatments.
Figure 2B:
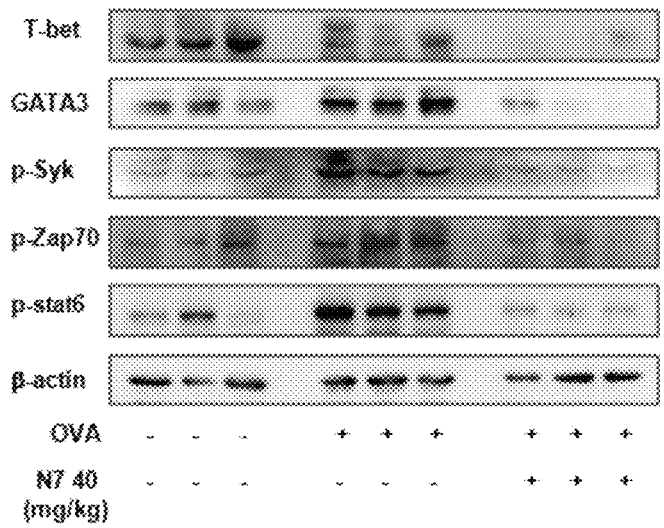
FIG. 2b shows the Western Blot analysis of the phosphorylation of Syk and other signal transduction proteins in murine spleen cells after different treatments.
Figure 2C:
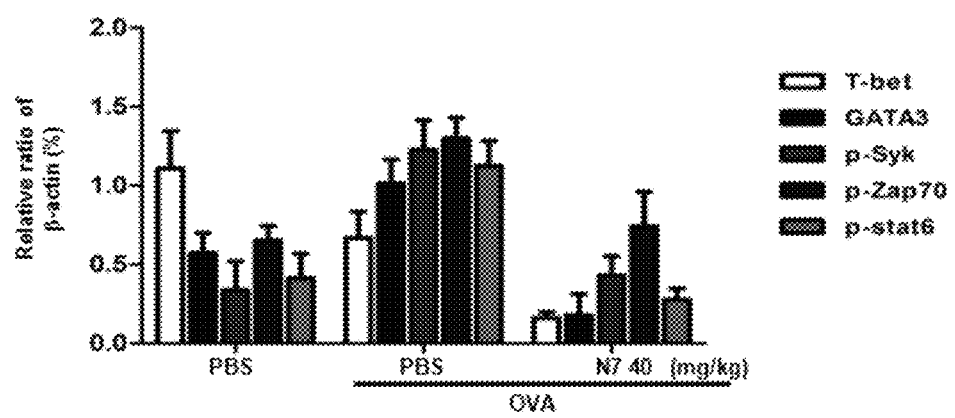
FIG. 2c compares the expressions of phosphorylated Syk, phosphorylated Zap70, phosphorylated stat6, T-bet and GATA3 in relative to β-actin expression as shown in FIG. 2b.

The experimental results are shown in FIGS. 2a to 2c. To obtain the data in FIG. 2a, murine spleen cells were grinded and treated with OVA for 3 days, and then the supernatants of the cell mixtures were collected for ELISA analysis. As discussed before, N7 can selectively inhibit the phosphorylation of Syk and therefore the effect of N7 on Syk in spleen cells was studied in this embodiment. As shown in FIG. 2b and FIG. 2c, the signal transduction proteins in spleen cells were detected. According to the experimental results, N7 inhibits the phosphorylation of Syk in spleen cells of mice having asthma.

Accordingly, Nujiangexanthone A inhibits the production of cytokines in spleen tissues and the expression of phosphorylated Syk, Zap70, Stat6 and GATA3 without altering the expression of T-bet.

Embodiment 3 Nujiangexanthone A (N7) Inhibits the Asthma Symptoms in Mice 3.1 Materials IgE kit purchased from Invitrogen Co., and OVA purchased from Sigma Co.

3.2 Methods 3.2.1 Asthma Model

Figure 3A:
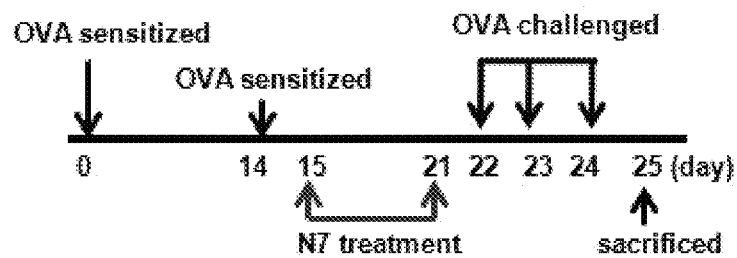
FIG. 3a shows a systematic diagram on setting up an asthma animal model.

Balb/c mice of SPF grade were selected for establishing an asthma animal model. With reference to FIG. 3a, ovalalbumin (OVA) dissolved in PBS with aluminum hydroxide gel was intraperitoneally injected to the mice to trigger systemic allergic responses, i.e. OVA sensitization. Then, atomized OVA was given to stimulate or challenge respiratory tracts of the mice. As such, a control group was prepared. By using the similar approach, treatment groups with an administration of N7 in different concentrations as well as a positive control group with an administration of dexamethasone were established. Also, a further control group of PBS was established by using same volume of PBS to replace OVA and using the PBS to replace the atomized OVA.

Symptoms of the mice were recorded during the test. Peripheral blood of the mice was collected before the end of the test so as to measure the release of IgE. Airway lavages were collected and the supernatants thereof were tested to measure the release of various cytokines. Cells were counted after being fixed and stained. The effect of Nujiangexanthone A on different types of immune cells was studied.

3.2.2 Statistical Analysis

Experimental data are all expressed by mean value±standard error. The data were analyzed by statistics software Graphpad Prism 5 with One-Way ANOVA analysis. Dunnet's test was used for pairwise comparisons. $P<0.05$ indicates a standard for statistically significant difference.

3.3 Results

Figure 3B:
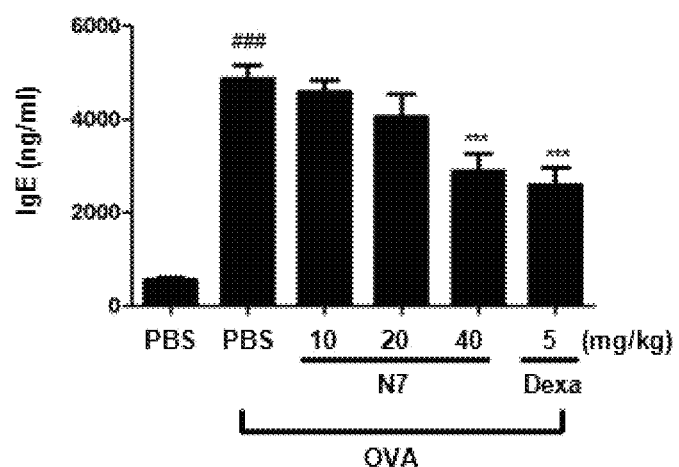
FIG. 3b shows the effect of N7 in inhibiting the expression of IgE in murine serum.
Figure 3C:
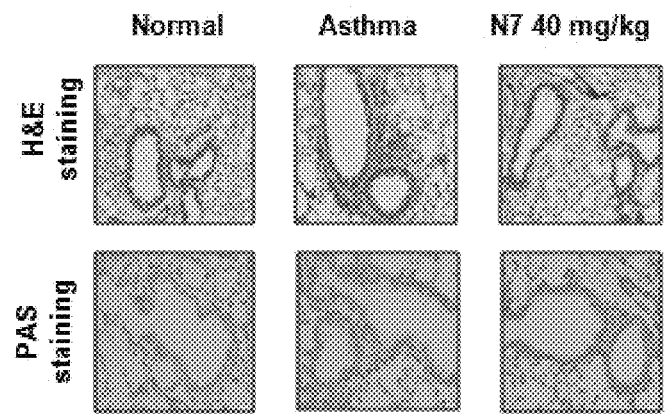
FIG. 3c shows murine lung tissues of a control group, an asthma model group and a N7 treated group stained by H&E and PAS dyes after treatments.
Figure 3D:
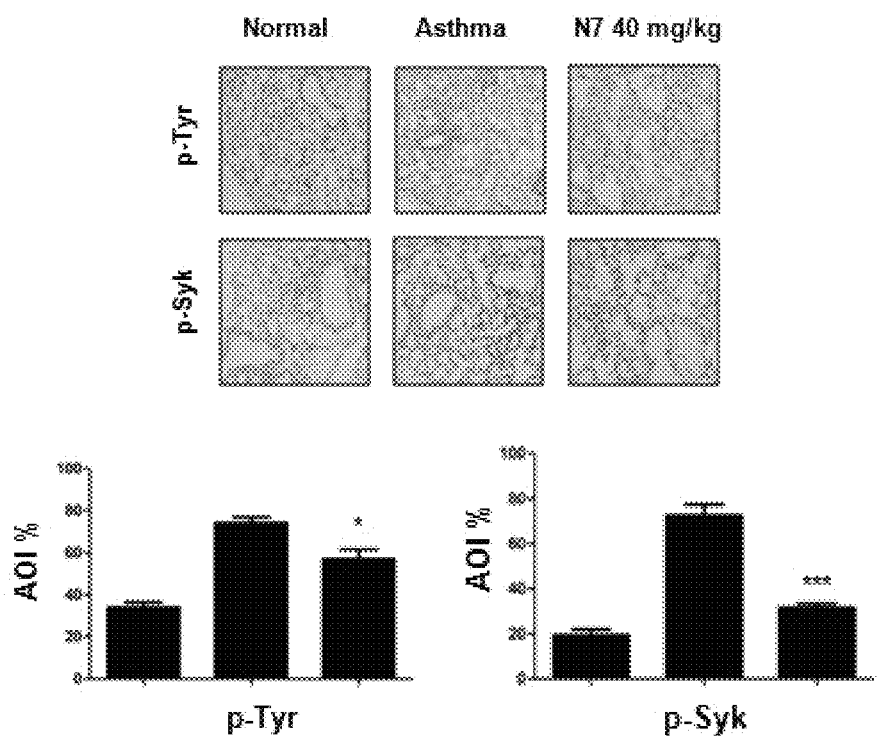
FIG. 3d shows murine lung tissues stained by immunohistochemistry showing the expressions of p-Syk and p-Tyr under different treatments, as compared with asthma group, *P<0.05; P<0.01; *P<0.001.

With reference to the results shown in FIGS. 3b to 3d, Nujiangexanthone A (N7) effectively inhibits the production of IgE in serum, and decreases infiltrates in peribronchial inflammatory cell. The results in FIG. 3d indicate that Nujiangexanthone A inhibits the level of phosphorylated tyrosine and phosphorylated Syk in lung tissues. Such results are consistent with the previous test results that N7 can selectively inhibit the phosphorylation of Syk.

Embodiment 4 Nujiangexanthone A (N7) Inhibits the Production of Cytokine in Peripheral Blood Mononuclear Cells (PBMC) of Asthma Patients 4.1 Materials Ficoll purchased from GE healthcare Co.

4.2 Methods 4.2.1 Sample Collection

Blood samples were collected from normal (healthy) people and people with asthma Peripheral blood mononuclear cells (PBMC) were isolated. By using Ficoll-density method, the effect of Nujiangexanthone A on the release of various cytokines in the isolated PBMCs was measured by qPCR.

4.2.2 Statistical Analysis

Experimental data are all expressed by mean value±standard error. The data were analyzed by statistics software Graphpad Prism 5 with One-Way ANOVA analysis. Dunnet's test was used for pairwise comparisons. $P<0.05$ indicates a standard for statistically significant difference.

4.3 Results

Figure 4:
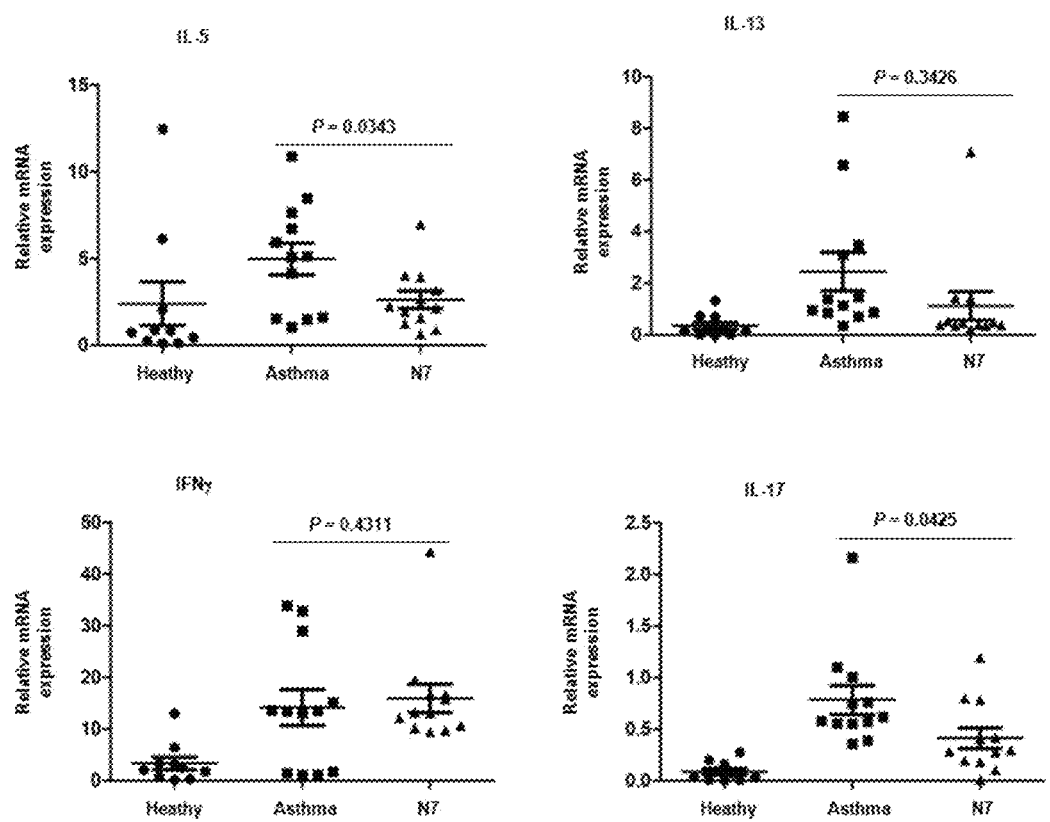
FIG. 4 shows the relative mRNA expressions of IL-3, IL-13, IFNγ and IL-17 in PBMCs of healthy people, asthma patients and asthma patients adminstered with N7, as compared with asthma patients, *P<0.05; P<0.01; *P<0.001.

The experimental results are shown in FIG. 4. Nujiangexanthone A (N7) inhibits the production of IL-5, IL-13, IL-17 in PBMC in asthma patients but does not inhibit the expression of IFN'.

Embodiment 5 Nujiangexanthone A (N7) Inhibits Signal Transduction Pathways of Jurkat Cells 5.1 Materials Human acute T cell leukemia, Jurkat cells, purchased from Institute of Cells of Shanghai Chinese Academy of Sciences.

24-well plate purchased from Denmark Thermo NUNC Co.

L15, fetal calf serum, penicillin and streptomycin purchased from Invitrogen Corporation.

5.2 Methods

Jurkat T cells were cultured in RPMI1640 containing 10% fetal calf serum, 100 U/ml of penicillin and 100 μg/ml of streptomycin. The cells were passed once every two days with fresh medium. After pretreating the cells with a medicament, PMA and ionomycin were used to treat the cells at different time points. After the treatments, the cells were collected for biomarker measurements.

Jurkat T cells culture: in a safe range of concentrations, cells were treated with Nujiangexanthone A in corresponding concentrations for 5, 15 and 30 minutes. The samples were collected and lysed. The samples were then separated by 8% gel in SDS-PAGE and transferred to PVDF membrane. The following antibodies were used to analyze the samples: ERK, JNK, p38, IKK, IkBa, NF-kB and so forth. If the compound is found to interfere with the expression and phosphorylation of the target proteins, a corresponding specific inhibitor may be used to conduct a comparative analysis.

5.3 Results

The effect of Nujiangexanthone A on the expression and phosphorylation of T cells signaling proteins was studied.

Figure 5A:
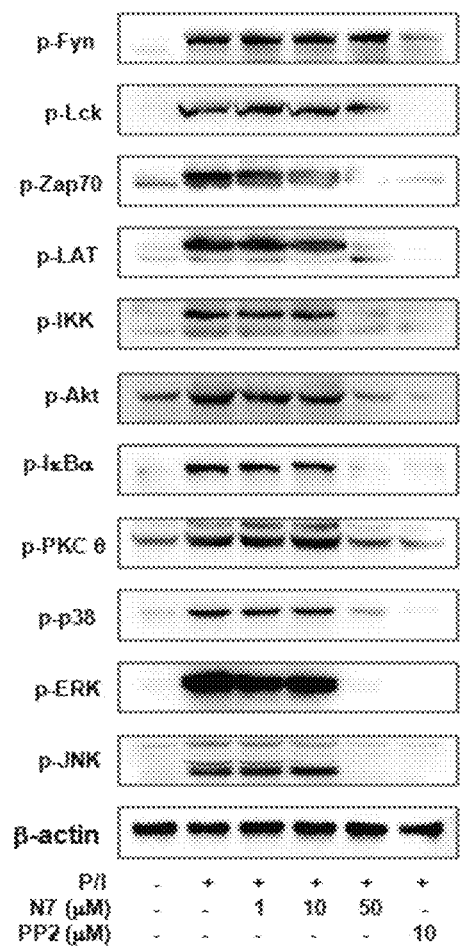
FIG. 5a shows the Western Blot analysis of proteins of T cells signaling transduction pathways after different treatments so as to determine the effect of N7 in inhibiting signal transduction pathways of Jurkat cells.
Figure 5B:
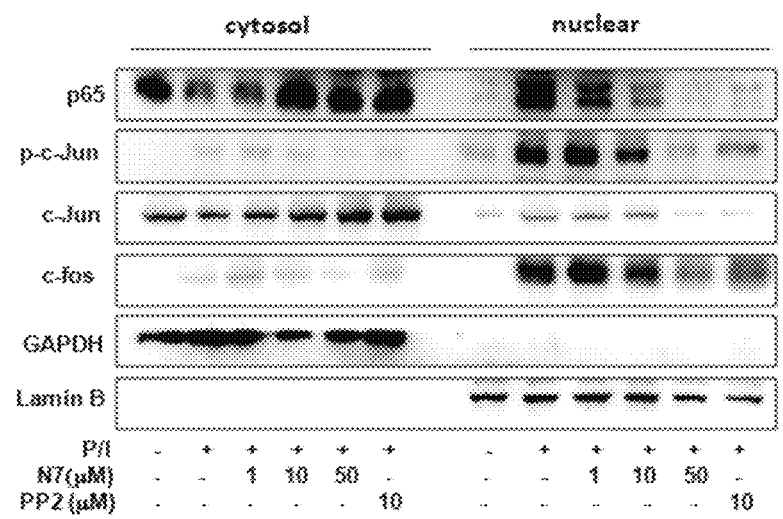
FIG. 5b shows Western Blot analysis of the cytosol and nuclear of Jurkat cells after different treatments.

In one test, Jurkat cells were pretreated with N7 and Src family inhibitor PP2 for 1 hour and then co-treated with PMA and ionomycin for 15 minutes. Then, a plurality of proteins of T cells signaling transduction pathways were measured by Western blot. As shown in FIG. 5a, N7 does not affect the phosphorylation of Fyn and Lck. Rather, N7 selectively inhibits the phosphorylation of Syk as well as various signal transduction pathway proteins that are downstream to Syk.

In a further test, Jurkat cells were pretreated with N7 and Src family inhibitor PP2 for 1 hour, and then co-treated with PMA and ionomycin for 30 minutes. The cytosol and nuclear of Jurkat cells were separated to measure the migration and phosphorylation of AP-1 and NF-kB.

Accordingly, the experimental results indicate that Nujiangexanthone A selectively inhibits phosphorylation of T cell upstream signaling molecule Syk without affecting Src family members Fyn and Lck (as shown in FIG. 5a). Syk, Fyn, and Lck are important signaling promoters to the upstream signaling of T cells. The phosphorylation of Syk can induce various downstream signal pathways such as MAPK, NF-kB and so forth. Fyn can stimulate Syk and Lck can stimulate Syk signal pathways. According to the results of the present invention, Nujiangexanthone A does not affect the phosphorylation of Fyn and Lck while significantly inhibits the phosphorylation of Syk, such that the downstream signal proteins of Syk such as MPK signaling pathways and NF-kB signaling pathways are inhibited.

Embodiment 6 Nujiangexanthone A (N7) Inhibits the Activation of Murine Mast Cells 6.1 Materials 96-well plate purchased from Thermo NUNC Co. in Denmark.

RPMI1640 (high glucose) fetal calf serum, penicillin and streptomycin purchased from Invitrogen Corporation in US.

6.2 Methods 6.2.1 Cell Culture

Murine BMMCs were isolated from BALB/c murine marrow and were cultured in a RPMI1640 medium containing IL-3, 10% of calf serum, 100 U/ml of penicillin and 100 μg/ml of streptomycin for 6 weeks. Two markers c-kit and FceRI on cell membranes were detected by using flow cytometric analysis. When double-positive cells detected, having both markers, have exceeded 95%, the cultured cells can be used for the experiment.

6.2.2 Cytokines Measurements

IgE mast cells were pretreated with IgE overnight and washed by PBS thrice. After re-suspended with medium, they were treated with different concentrations of Nujiangexanthone A for 1 hour. DNP-HAS or antigen was then used to treat the cells for 6 hours. The supernatants were collected for measurement. The amounts of TNF-α and IL-6 were measured by an ELISA kit.

6.2.3 Detection of LTC4, $Ca^{2+}$ and Degranulation

IgE mast cells were pretreated with IgE overnight and washed by PBS thrice. After re-suspended with medium, they were treated with different concentrations of Nujiangexanthone A for 1 hour. DNP-HAS or antigen was then used to treat the cells for 15 minutes. The supernatants were collected for measurement. The amounts of LTC4 and $Ca^{2+}$ as well as the degranulation response were measured by an ELISA kit.

The amount of b-Hex was measured to evaluate the degranulation response.

Also, the amount of PGD2 was also measured by the above approach except that the antigen was used to treat the cells for 7 hours before any measurement.

6.2.4 Statistical Analysis

Experimental data are all expressed by mean value±standard error. The data were analyzed by statistics software Graphpad Prism 5 with One-Way ANOVA analysis. Dunnet's test was used for pairwise comparisons. $P<0.05$ indicates a standard for statistically significant difference.

6.3 Results

Figure 6:
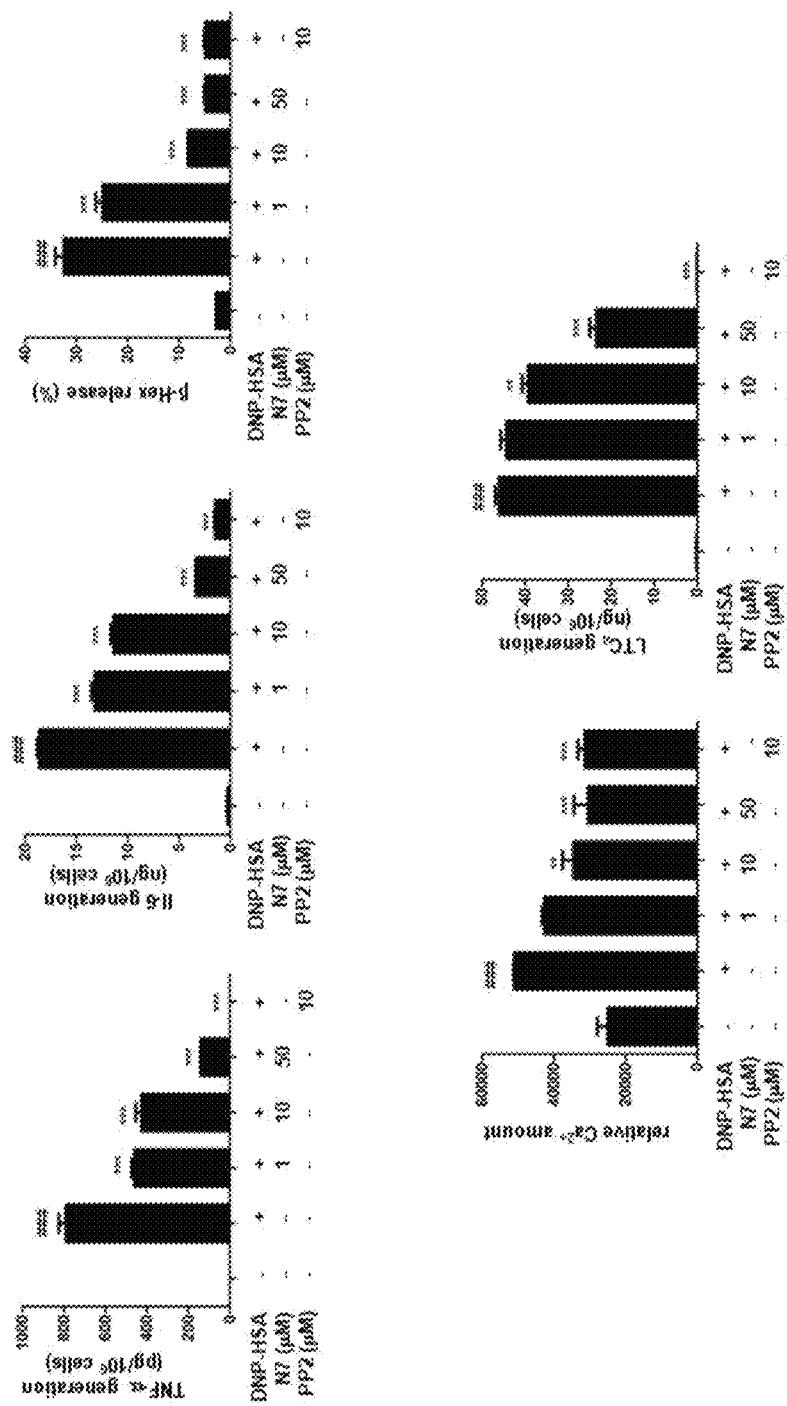
FIG. 6 shows the ELISA analysis on TNF-α, IL-6, β-Hex, $Ca^{2+}$ and LTC4 so as to determine the production of cytokines TNF-α, IL-6, degranulation of mast cells, concentrations of calcium and the production of leukotriene under the treatments of N7, DNP-HAS and PP2, as compared with the solvent group, *P<0.05; P<0.01; *P<0.001.

With reference to the results shown in FIG. 6, Nujiangexanthone A (N7) is found to inhibit the production of cytokines such as TNF-α and IL-6, inhibit degranulation of mast cells, lower the concentration of calcium and inhibit the production of leukotriene LTC4, within a range of concentration having no cytotoxicity. These effects are found to be dose-dependent.

Embodiment 7 Nujiangexanthone A (N7) Inhibits the Production of Cytokines in Lung Tissue 7.1 Materials IL-4, IL-5, IL-13, eotaxin, IFNγ, PGD2 and LTC4 assay kits purchased from Invitrogen Ltd.

7.2 Methods 7.2.1 Tissue Collection

Some portions of lung tissue of the animal models were collected to evaluate lung inflammatory status. A portion of the collected lung tissue was isolated to extract RNA, and another portion of the lung tissue was grinded and digested for cytokines measurements.

7.2.2 Statistical Analysis

Experimental data are all expressed by mean value±standard error. The data were analyzed by statistics software Graphpad Prism 5 with One-Way ANOVA analysis. Dunnet's test was used for pairwise comparisons. $P<0.05$ indicates a standard for statistically significant difference.

7.3 Results

Figure 7:
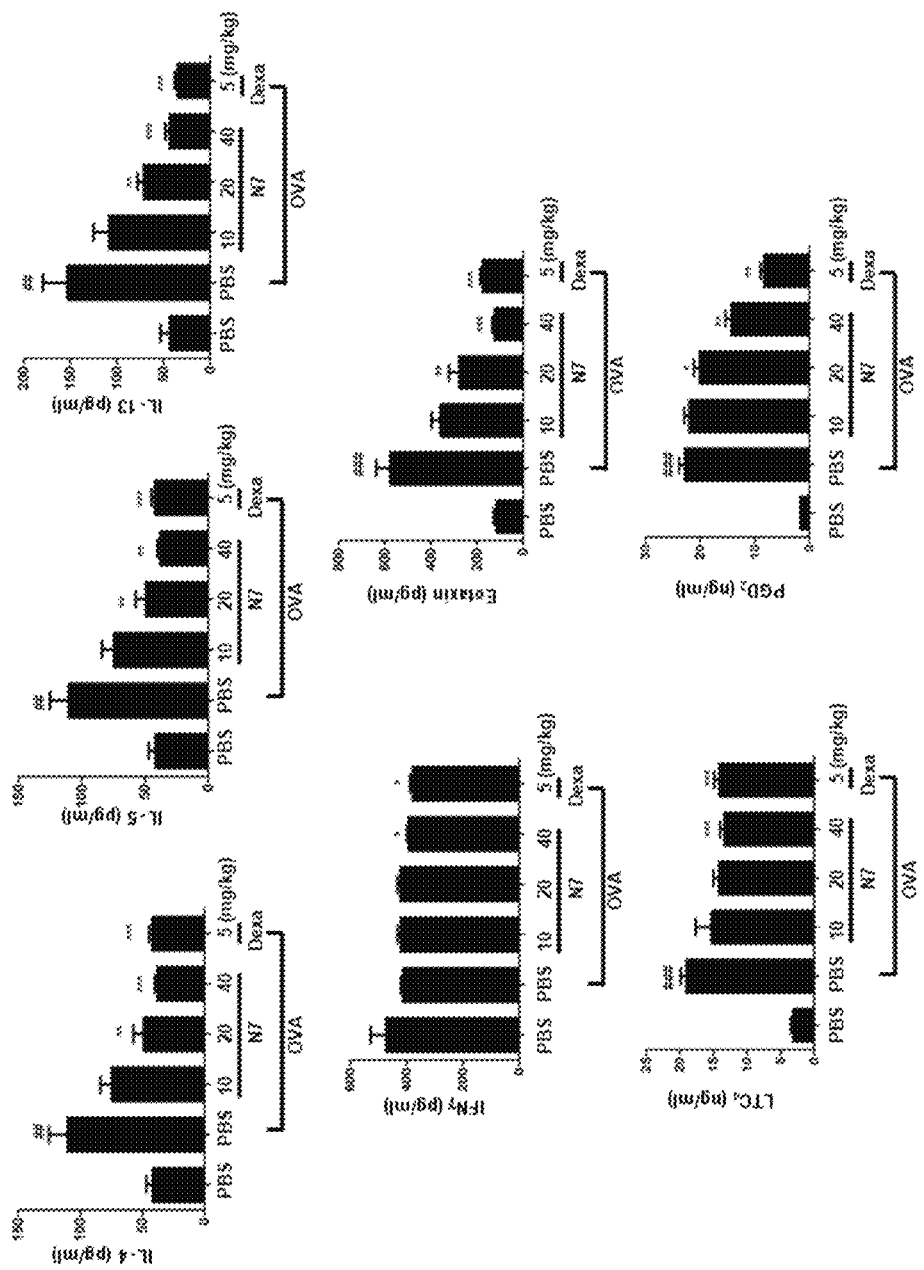
FIG. 7 shows the amounts of cytokines IL-4, IL-5, IL-13, IFNγ, eotasin, LTC4 and PGD2 in murine lung cells under different treatments, as compared with asthma model group, *P<0.05; P<0.01; *P<0.001.

With reference to FIG. 7, the Nujiangexanthone A (N7) inhibits the production of cytokines such as IL-4, IL-5, IL-13, eotaxin, PGD2 and LTC4 in lung tissue. However, Nujiangexanthone A does not affect the production of IFNγ.

As Nujiangexanthone A is found to inhibit the production of cytokines, it can prevent asthma.

Various aspects of the present invention are described above. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for treating asthma in a subject having asthma, comprising: administering an effective amount of a compound of formula (I) or a pharmaceutically acceptable salt or hydrate thereof to the subject

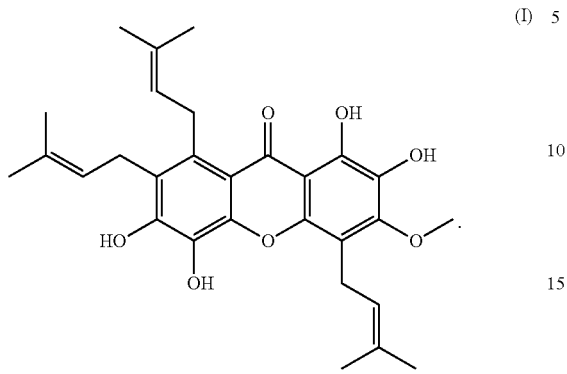

(I)

2. The method according to claim 1, wherein the effective amount of the compound is administered directly to a mast cell of the subject.

3. The method according to claim 1, wherein the compound is administered in the form of a pharmaceutical composition that contains about 0.0001-50 wt % of the compound.

4. The method according to claim 3, wherein the composition is administered to the subject at a dosage of 0.001-50 mg/kg body weight/day.

* * * * *